United States Patent [19]

Suenobu et al.

[11] 4,319,051

[45] Mar. 9, 1982

[54] TRISPHENOL HYDRATE

[75] Inventors: Koreyoshi Suenobu, Buzen; Eizaburo Kaku, Kashihara; Takanori Miura, Yoshitomi, all of Japan

[73] Assignee: Yoshitomi Pharmaceutical Industries, Ltd., Osaka, Japan

[21] Appl. No.: 185,852

[22] Filed: Sep. 10, 1980

[30] Foreign Application Priority Data

Sep. 10, 1979 [JP] Japan .................... 54-116361

[51] Int. Cl.³ ............................................ C07C 39/16
[52] U.S. Cl. .................................................... 568/720
[58] Field of Search ............... 568/720, 722, 749, 753

[56] References Cited

U.S. PATENT DOCUMENTS 3,196,185  7/1965  Ranson .................................. 568/720

FOREIGN PATENT DOCUMENTS 951935  3/1964  United Kingdom ................ 568/720

*Primary Examiner*—Werren B. Lone
*Attorney, Agent, or Firm*—Sughrue, Mion, Zinn, Macpeak and Seas

[57] ABSTRACT

1,1,3-Tris(2-methyl-4-hydroxy-5-tert-butylphenyl)-butane hydrate is provided which can easily be prepared and is free from any organic solvents that may present odor and health hazard problems.

2 Claims, No Drawings

TRISPHENOL HYDRATE

BACKGROUND OF THE INVENTION

1. Field of the Invention

This invention relates to a novel trisphenol hydrate. More particularly, it relates to 1,1,3-tris(2-methyl-4-hydroxy-5-tert-butylphenyl)butane hydrate which melts at much lower temperatures than the melting point of 1,1,3-tris(2-methyl-4-hydroxy-5-tert-butylphenyl)butane.

2. Description of the Prior Art 1,1,3-Tris(2-methyl-4-hydroxy-5-tert-butylphenyl)butane is in wide use as an antioxidant for such high-molecular substances as natural and synthetic rubbers, polyethylene, polypropylene, other polyolefins, polystyrene, polyesters, poly(vinyl chloride) and ABS (acrylonitrile-butadiene-styrene) resins. According to U.S. Pat. No. 3,196,185, for instance, this compound is produced by condensation of crotonaldehyde and 3-methyl-6-tert-butylphenol and recrystallized from toluene, whereby a crystalline product having a melting point of 180°–182° C. is obtained. As desired, this product is recrystallized from petroleum ether (boiling point: 80°–100° C.) and dried under high vacuum at 100° C. for several hours, whereby a product melting (with decomposition) at 188° C. is obtained.

However, when such a purification method is employed, the crystalline product prepared by recrystallization from toluene, for instance, naturally and characteristically contains a considerable amount of toluene. Use of such a product as it is as an antioxidant is undesirable from the viewpoints of odor and health hazard. Although heating at 120° C. for 3 hours, for instance, can eliminate the toluene, such heating may undesirably cause discoloration of the product.

SUMMARY OF THE INVENTION

The present inventors have made intensive studies to avoid the above drawbacks and have now found that 1,1,3-tris(2-methyl-4-hydroxy-5-tert-butylphenyl)butane hydrate not only exhibits an antioxidant activity comparable to that of 1,1,3-tris(2-methyl-4-hydroxy-5-tert-butylphenyl)-butane (anhydrous or toluene-containing) but also is free from the drawbacks mentioned above.

DETAILED DESCRIPTION OF THE INVENTION

The hydrate of the invention does not contain any organic solvent at all but contains about 3 molecules of water of crystallization. It can be prepared in a simple and easy manner as will be described later without requiring much labor for removing the organic solvent by heating.

While 1,1,3-tris(2-methyl-4-hydroxy-5-tert-butylphenyl)-butane has a melting point of about 182° C., the hydrate of the invention melts at about 125°–130° C., releasing the water of crystallization. After completion of the water release, it solidifies at about 160°–170° C. and again melts at 187°–197° C.

The hydrate of the invention is somewhat higher in solubility in methanol than the toluene-containing trisphenol. This fact is favorable when the hydrate is to be added to poly(vinyl chloride), ABS resins, MBS resins (M: methyl methacrylate) and other resins which are produced by emulsion or suspension polymerization using aqueous media, because the antioxidant is usually added to the polymerization systems for said resins in the form of a solution in such an organic solvent as methanol.

Another feature of the invention is that the preparation of the hydrate of the invention does not require such troublesome purification procedure as recrystallization from toluene as described in U.S. Pat. No. 3,196,185. The hydrate of the invention can be produced by washing the crude product of condensation of crotonaldehyde and 3-methyl-6-tert-butylphenol in a molar ratio of 1:3 with aqueous methanol to remove byproducts, followed by treating with water.

The following example and test examples illustrate the invention in more detail.

EXAMPLE

Crotonaldehyde (140 g, 2 moles) is gradually added dropwise to a stirred mixture of 984 g (6 moles) of 3-methyl-6-tert-butylphenol, 700 g of methanol and 350 ml of concentrated hydrochloric acid under gentle refluxing. Refluxing is then continued for an hour. The reaction mixture is cooled, and the precipitate is collected by filtration, washed first with 2,000 ml of 80% methanol to remove byproducts and unreacted starting materials contained in the precipitate and then with water until no inorganic substances can be detected any longer, and dried at 65°–70° C. for 5 hours, to give 903 g of 1,1,3-tris(2-methyl-4-hydroxy-5-tert-butylphenyl)-butane hydrate.

The product contains about 3 molecules of water of crystallization and melts at 125°–127° C. The water of crystallization can be eliminated by drying under melting; the dried product has a melting point of 188°–190° C.

TEST EXAMPLE 1

The hydrate prepared by the procedure of the above example was tested for antioxidant efficiency in polypropylene.

Thus, the additives shown in Table 1 were respectively added in given amounts to 100 parts by weight of polypropylene powder. Each mixture was pelletized at 280° C. The pellets obtained were evaluated macroscopically for color and tested for melt index (MI, in grams per 10 min.) in accordance with JIS K-6758 (Testing Methods for Polypropylene).

The above pellets were compression molded (preheating: 200° C.×15 min.; press pressure: 100 kg/cm²) into sheets, 0.5 mm in thickness and 40×80 mm in size. The sheets were placed in a Gear type aging tester maintained at 150° C. and the time to failure (crumbling on any part of the specimen) was determined.

The results of the above tests are summarized in Table 1.

TABLE 1

| No. | Additive system Compound | Amount (part) | MI | Time to failure (hours) |
|---|---|---|---|---|
| 1 | 1,1,3-Tris(2-methyl-4-hydroxy-5-tert-butylphenyl)butane hydrate | 0.3 | 17.9 | 320 |
| 2 | 1,1,3-Tris(2-methyl-4-hydroxy-5-tert-butylphenyl)butane | 0.3 | 18.0 | 320 |
| 3 | 1,1,3-Tris(2-methyl-4-hydroxy-5-tert-butylphenyl)butane hydrate plus | 0.1 | 9.4 | 740 |

TABLE 1-continued

| No. | Additive system Compound | Amount (part) | MI | Time to failure (hours) |
|---|---|---|---|---|
| | Dimyristyl thiodipropionate | 0.2 | | |
| 4 | 1,1,3-Tris(2-methyl-4-hydroxy-5-tert-butylphenyl)butane plus | 0.1 | 9.5 | 740 |
| | Dimyristyl thiodipropionate | 0.2 | | |

In Table 1, additive systems Nos. 1 and 3 are for the invention, while Nos. 2 and 4 are for comparison. The 1,1,3-tris(2-methyl-4-hydroxy-5-tert-butylphenyl)butane used for comparison was an anhydrous one which was also free from toluene.

There were observed no differences in color between the pellets containing additive system No. 1 and those containing additive system No. 2 or between the pellets containing additive system No. 3 and those containing additive system No. 4.

TEST EXAMPLE 2

The hydrate of the invention was tested for color stability on heating.

Thus, the hydrate sample was placed in a capillary and heated at 190° C. After 3 hours and 5 hours of heating, the degree of discoloration (browning) was evaluated macroscopically. The results are set forth in Table 2.

TABLE 2

| | | Discoloration after | |
|---|---|---|---|
| No. | Compound | 3 hours | 5 hours |
| 1 | 1,1,3-Tris(2-methyl-4-hydroxy-5-tert-butylphenyl)butane hydrate | Slight | Medium (pale brown) |
| 2 | Product of recrystallization from toluene (toluene-containing) | Medium (pale brown) | Remarkable (brown) |
| 3 | Product of recrystallization followed by heating for removal of toluene | Remarkable (brown) | Very remarkable (dark brown) |

In the above table, compound No. 1 is the compound of the invention, while compound No. 2 and compound No. 3 are the compounds in accordance with U.S. Pat. No. 3,196,185.

What is claimed is:
1. 1,1,3-Tris(2-methyl-4-hydroxy-5-tert-butylphenyl)butane trihydrate.
2. An antioxidant which consists of 1,1,3-tris(2-methyl-4-hydroxy-5-tert-butylphenyl)butane trihydrate.

* * * * *